(12) United States Patent
Cooper et al.

(10) Patent No.: US 6,884,575 B2
(45) Date of Patent: Apr. 26, 2005

(54) PHOSPHOPROTEIN TARGET FOR INSULIN AND ITS ANTAGONISTS

(75) Inventors: Garth J. S. Cooper, Auckland (NZ); Aimin Xu, Auckland (NZ); Yu Wang, Auckland (NZ)

(73) Assignee: Protemix Corporation Limited, Auckland (NZ)

( * ) Notice: Subject to any disclaimer, the term of this patent is extended or adjusted under 35 U.S.C. 154(b) by 279 days.

(21) Appl. No.: 10/114,540

(22) Filed: Apr. 1, 2002

(65) Prior Publication Data

US 2002/0197596 A1 Dec. 26, 2002

Related U.S. Application Data

(60) Provisional application No. 60/280,584, filed on Mar. 30, 2001.

(51) Int. Cl.[7] .................................................. C12Q 1/00
(52) U.S. Cl. .......................................................... 435/4
(58) Field of Search ........................ 435/4, 7.1; 530/350; 514/2

(56) References Cited

PUBLICATIONS

Wang et al., "Insulin And Insulin Antagonists Evoke Phosphorylation Of P20 at Serine 157 and Serine 16 Respectively in Rat Skeletal Muscle", FEBS Letters 462 (1999) 25–30.
Wang et al., "Amylin Evokes Phosphorylation of P20 in Rat Skeletal Muscle", FEBS Letters 457 (1999) 149–152.
Wang et al., "Phosphorylation of P20 Is Associated with the Actions of Insulin in Rat Skeletal and Smooth Muscle", Biochem. J. (1999) 344, 971–976 (Printed in Great Britain).
Wang et al., "Alteration in Phosphorylation of P20 Is Associated with Insulin Resistance", Diabetes, vol. 50, Aug. 2001, 1821–1827.
Andrews, R.C. and Walker, B.R. (1999). "Glucocorticoids and insulin resistance: old hormones, new targets," Clin. Sci. 96:513–523.
Beall, A.C. et al. (1997). "Cyclic nucleotide–dependent vasorelaxation is associated with the phosphorylation of a small heat shock–related protein," J. Biol. Chem. 272:11283–11287.
Bergman, R.N. et al. (1985). "Assessment of insulin sensitivity in vivo," Endocrine Review 6:45–86.
Bjornholm, M. et al. (1997). "Insulin receptor susbstrate–1 phosphorylation and phosphatidylinositol 3–kinase activity in skeletal muscle from NIDDM subjects after in vivo insulin stimulation," Diabetes 46:524–527.
Bjorntorp, P. (1999). "Neuroendocrine perturbations as a cause of insulin resistance," Diabet/Metab Res. Rev. 15:427–441.
Boden, G. (1998). "Free fatty acids (FFA), a link between obesity and insulin resistance," Front. Biosci. 3:D169–D175.

Brophy, C.M. et al. (1999). "The small heat shock–related protein–20 is an actin–associated protein," J. Vasc. Surg. 29:326–333.
Castle, A.L. (1998), "Amylin influences insulin–stimulated glucose metabolism by two independent mechanisms," Am. J. Physiol. 274:E6–E12.
Christopoulos, G. et al. (1999). "Multiple amylin receptors arise from receptor activity–modifying protein interaction with the calcitonin receptor gene product," Mol. Pharmacol. 56:235–242.
Condorelli, G. et al. (1998). "PED/PEA–15 gene controls glucose transport and is overexpressed in type 2 diabetes mellitus," ENMO J 17:3858–3866.
Cooper, G.J.S. (1994). "Amylin compared with calcitonin gene–related peptide: structure, biology, and relevance to metabolic disease," Endocr. Rev. 15:163–201.
Cooper, G.J.S. et al. (1998). "Amylin found in amyloid deposits in human type 2 diabetes mellitus may be a hormone that regulates glycogen metabolism in skeletal muscle," Proc. Natl. Acad. Sci. USA 85:7763–7766.
DeFronzo, R.A. (1997). "Pathogenesis of type 2 diabetes: metabolic and molecular implications for identifying diabetes genes," Diabet. Rev. 5:177–269.
Dimitriadis, G. et al. (1997). "Effects of glucocorticoid excess on the sensitivity of glucose transport and metabolism to insulin in rat skeletal muscle," Biochem. J. 321:707–712.
Enoki, S. et al. (1992). "Plasma islet amyloid polypeptide levels in obesity, impaired glucose tolerance and non–insulin–dependent diabetes mellitus," Diabet. Res. Clin. Prac. 15:97–102.
Fodor, S.P.A. et al. (1991). "Light–directed, spatially addressable parallel chemical synthesis," Science 251:767–773.
Folli, F. (1993). "Regulation of phosphatidylinositol 3–kinase activity in liver and muscle of animal models of insulin–resistant and insulin–deficient diabetes mellitus," J. Clin. Invest. 92:1787–1794.
Frontoni, S et al. (1991). "In vivo insulin resistance induced by amylin primarily through inhibition of insulin–stimulated glycogen synthesis in skeletal muscle," Diabetes 40:568–573.
Gebre–Medhin, S. et al. (1998). "Increased insulin secretion and glucose tolerance in mice lacking islet amyloid polypeptide (amylin)," Biochern. Biophys. Res. Commun. 250:271–277.
Gennaro, A.R. (Ed.)(1995). Remington Pharmaceutical Sciences 19th Ed. Mack Publishing (Table of Contents) pp. xv–xvi.
Giorgino, F. (1993). "Glucocorticoid regulation of insulin receptor and substrate IRS–1 tyrosine phosphorylation in rat skeletal muscle in vivo," J. Clin. Invest 91:2020–2030.
Gold, L. (1995). "Oligonucleotides as research, diagnostic, and therapeutic agents," J. Biol. Chem. 270:13581–13584.

(Continued)

Primary Examiner—Karen Cochrane Carlson
Assistant Examiner—Sheridan Snedden
(74) Attorney, Agent, or Firm—Buchanan Ingersoll LLP (57) ABSTRACT

The invention provides methods for diagnosing and treating individuals with insulin resistance.

16 Claims, 7 Drawing Sheets

OTHER PUBLICATIONS

Hettiarachchi, M. et al. (1997). "Rat amylin (8–37) enhances insulin action and alters lipid metabolism in normal and insulin resistant rats," *Am. J. Physiol.* 273:E859–E867.

Hunter, S.J. and Garvey, W.T. (1998). "Insulin action and insulin resistance: diseases involving defects in insulin receptors, signal transduction, and the glucose transport effector system," *Am. J. Med.* 105:331–345.

Inaguma, Y. et al. (1996). "cDNA cloning of a 20–kDa protein (p20) highly homologous to small heat shock proteins: developmental and physiological changes in rat hindlimb muscles," *Gene* 178(1–2):145–150.

Kahn, B.B. (1998). "Type 2 diabetes: When insulin secretion fails to compensate for insulin resistance," *Cell* 92:593–596.

Kahn, C.R. (1994). "Insulin action, diabetogenes, and the cause of type II diabetes," *Diabetes* 43:1066–1084.

Kao, A.W. (1999). "Aldolase mediates the association of F–actin with the insulin–responsive glucose transporter GLUT4," *J. Biol. Chem.* 274:17742–17747.

Kato, K. (1994). "Purification and characteristization of a 20–kDa protein that is highly homologous to alpha B crystallin," *J. Biol. Chem.* 269:15302–15309.

Lam, K.S. (1997) "Application of combinatorial library methods in cancer research and drug discovery," *Anticancer Drug Des.* 12:145–167.

Leighton, B. and Cooper, G.J. (1988). "Pancreatic amylin and calcitonin gene–related peptide cause resistance to insulin in skeletal muscle in vitro," *Nature* 335:632–635.

Molina, J.M. et al. (1990). "Induction of insulin resistance in–vivo by amylin and calcitonin gene–related peptide," *Diabetes* 39:260–265.

Moller, D.E. and Flier, J.S. (1991). "Insulin resistance—mechanisms, syndromes, and implications," *N. Engl. J. Med.* 325:938–948.

Moller, D.E. et al. (1996). "Candidate genes for insulin resistance," *Diabet. Care* 19:396–400.

Moyers, J.S. et al. (1996). "Overexpression of Rad inhibits glucose uptake in cultured muscle and fat cells," *J. Biol. Chem.* 271:23111–23116.

Niwa, M. et al. (2000). "Small molecular weight heat shock–related protein, HSP20, exhibits an anti–platelet activity by inhibiting receptor–mediated calcium influx," *Life Sci.* 66:L7–L12.

Oakes, N.D. et al. (1997). "Mechanisms of liver and muscle insulin resistance induced by chronic high–fat feeding," *Diabetes* 46:1768–1774.

Peraldi, P. and Spiegelman, B. (1998). "TNF–alpha and insulin resistance: Summary and future prospects," *Mol. Cell Biochem.* 182:169–175.

Pieber, T.R. et al. (1993). "Amylin–insulin relationships in insulin resistance with and without diabetic hyperglycemia," *Am. J. Physiol.* 265:E446–E453.

Reaven, G.M. (1995). "Pathophysiology of insulin resistance in human disease," *Physiol. Rev.* 75:473–486.

Reaven, G.M. and Miller, R.G. (1979). "An attempt to define the nature of chemical diabetes using a multidimensional analysis," *Diabetologia* 16:17–24.

Robinson, R. et al. (1993). "Glucose transport in L6 myoblasts overexpressing GLUT1 and GLUT4," *J. Biol. Chem.* 268:22119–22126.

Suh, N. et al. (1995). "Discovery of natural product chemopreventive agents utilizing HL–60 cell differentiation as a model," *Anticancer Res.* 15(2):233–239.

Tsakiridis, T. et al. (1994). "Disassembly of the actin network inhibits insulin–dependent stimulation of glucose transport and prevents recruitment of glucose transporters to the plasma membrane," *J. Biol. Chem.* 269:29934–29942.

Turner, D.M. (1996). "Natural product source material use in the pharmaceutical industry: the Glaxo experience," *J. Ethnopharmacol.* 51(1–3):39–44.

van Breemen, R.B. et al. (1997). "Pulsed ultrafiltration mass spectrometry: a new method for screening combinatorial libraries," *Anal. Chem.* 69:2159–2164.

Wang, Y. (2001). "Alteration in phosphorylation of P20 is associated with Insulin Resistance," *Diabetes* 50:1821–1827.

Wang, Y. et al. (1999). "Amylin evokes phosphorylation of P20 in rat skeletal muscle," *FEBS Lett.* 457:149–152.

Wang, Y. et al. (1999). "Insulin and insulin antagonists evoke phosphorylation of P20 at serine 157 and serine 16 respectively in rat skeletal muscle," *FEBS Lett.* 462:25–30.

Wang, Y. et al. (1999). "Phosphorylation of P20 is associated with the actions of insulin in rat skeletal and smooth muscle," *Biochem. J.* 344:971–976.

Woodrum, D.A. et al. (1999), "Phosphorylation events associated with cyclic nucleotide–dependent inhibition of smooth muscle contraction," *Am. J. Physiol.* 277:H931–H939.

Young, A.A. et al. (1991). "Amylin injection causes elevated plasma lactate and glucose in the rat," *FEBS Lett.* 291:101–104.

Young, D.A. (1990). "Effects of amylin on glucose metabolism and glycogenolysis in vivo and in vitro," *Am. J. Physiol.* 259:E457–E461.

|              | S1       | S2         | S3         |
|--------------|----------|------------|------------|
| Healthy rats | 468 ± 21 | 22.3 ± 2.1 | 19.6 ± 1 4 |
| High fat rats| 476 ± 30 | 124 ± 7 1* | 136 ± 9.8* |

PHOSPHOPROTEIN TARGET FOR INSULIN AND ITS ANTAGONISTS

CROSS REFERENCE TO RELATED APPLICATIONS

This application claims benefit of U.S. provisional application No. 60/280,584, filed on Mar. 30, 2001, the contents of which are hereby incorporated by reference herein.

TECHNICAL FIELD

The invention relates to the field of proteomics. More specifically, it relates to a phosphoprotein target that exhibits distinct phosphorylation patterns in response to insulin and its antagonists and in certain disease states.

BACKGROUND OF THE INVENTION

Publications referred to by reference numbering in this specification correspond to the reference list at the end of the specification.

Insulin resistance is characterised by diminished insulin sensitivity of target tissues including liver, skeletal muscle and adipocytes (1). It is a key factor in the pathogenesis of type II diabetes mellitus and is also associated with other pathological states, such as obesity, dyslipidaemia, hyperinsulinaemia, hypertension and cardiovascular disease. These clustering metabolic defects have been termed syndrome X" or "the insulin resistance syndrome" (2).

The molecular basis of insulin resistance is extremely complex and multifactorial. Defects in several steps of insulin action, such as the activation of insulin receptors, post-receptor signal transduction and the glucose transport effector system, have been implicated in this disease (3, 4). Defective insulin receptor kinase activity, reduced IRS-1 tyrosine phosphorylation and decreased PI-3 kinase activity were observed in both human type II diabetic patients as well as animal models such as ob/ob mice (5, 6).

In addition to the intrinsic defects of the insulin receptor and postreceptor signalling components, other circulating factors, such as TNF-α, leptin, free fatty acids (FFA) and amylin may also contribute to the pathogenesis of insulin resistance (7–11). For instance, amylin, a hormone co-secreted with insulin from pancreatic islet β-cells, has been shown to antagonise insulin's metabolic actions both in vivo and in vitro (12–16). It can inhibit insulin-stimulated glucose uptake and glycogen synthesis. In vivo administration of amylin resulted in hyperglycemia and induced insulin resistance, similar to that observed in type II diabetes. Although some earlier studies suggested that amylin's biological effects on fuel metabolism were only of pharmacological interest, more recent in vivo studies with an amylin-selective antagonist have strongly supported its physiological relevance (17). Moreover, amylin deficient mice showed increased insulin responsiveness and more rapid blood glucose elimination following glucose loading, further confirming the role of amylin in the causation of insulin resistance (18). Indeed, elevated levels of circulating amylin (hyperamylinemia) and an increased ratio of amylin to insulin were observed in patients with type II diabetes as well as other diseases associated with insulin resistance, such as obesity and glucose intolerance (19).

Despite these advances, the detailed cellular mechanisms of insulin resistance are far from clear and there is a need for new therapeutic and diagnostic modalities for this condition.

SUMMARY OF THE INVENTION

The invention provides, in one aspect, a method for screening for an agent useful for treatment of insulin resistance by contacting a mammalian cell expressing P20 and the agent and determining if the agent suppresses the level of at least one of P20 isoforms S2 and S3, wherein the suppression of S2 and S3 levels is indicative of an agent useful for treatment of insulin resistance. In one embodiment, the mammalian cell is insulin resistant. In another embodiment, the mammalian cell is from a rat or human. In another embodiment, the mammalian cell is a myocyte, adipocyte, or skeletal muscle cell. In another embodiment, the agent is contacted with isolated skeletal muscle. In another embodiment, the contacting occurs by administration of the test agent to an animal (e.g., a rodent with genetic or experimentally induced insulin resistance). In another embodiment, the cell is exposed to an amount of amylin, CGRP1, CGRP2, epinephrine or norepinephrine sufficient to induce phosphorylation of P20 during, prior to, or after contacting the cell and the test agent. In another embodiment, the cell is exposed to an amount of insulin sufficient to reduce amylin-induced phosphorylation of P20 in a non-insulin resistant cell, during, prior to, or after contacting the cell and the test agent. In another embodiment, the cell is exposed to insulin ex vivo.

In another aspect, the invention provides a method for screening for an agent useful for treatment of insulin resistance by: (a) contacting an insulin resistant mammalian cell expressing P20 and the agent; (b) determining an expression level of at least one of P20 isoforms expression level of S2 or S3, wherein said reference expression level is characteristic of (i) expression in a similar cell not exposed to the agent or (ii) expression in a cell that is not insulin resistant, and wherein an expression level that is lower than (i) or similar to (ii) indicates the agent is useful for treatment of insulin resistance. In one embodiment, the mammalian cell is from a rat or human. In another embodiment, the mammalian cell is a myocyte, adipocyte, or skeletal muscle cell. In another embodiment, the agent is contacted with isolated skeletal muscle. In another embodiment, the contacting occurs by administration of the test agent to an animal (e.g., rodent with genetic or experimentally induced insulin resistance)

In another aspect, the invention provides a method for diagnosing insulin resistance in an individual by obtaining a biological sample from the individual and determining a level of at least one of P20 isoforms S2 and S3, wherein the individual is diagnosed as being insulin resistant when the level of expression of at least one of S2 and S3 is higher than a reference level characteristic of an individual not suffering from insulin resistance. In one embodiment, the cells in the biological sample are contacted with insulin ex vivo. In another embodiment, the levels of both S2 and S3 are determined. In another embodiment, the levels of both S2 and S3 are higher than a reference level characteristic of an individual not suffering from insulin resistance.

In another aspect, the invention provides a method of treating insulin resistance in an individual comprising administering a treatment or an agent that reduces the level of P20 isoforms S2 and S3 in the individual. In one embodiment, the agent is identified by the methods of screening described above.

In another aspect, the invention provides the use of an agent that reduces the level of at least one of S2 and S3 in a cell in the preparation of a medicament for treatment of insulin resistance.

In another aspect, the invention provides a method of assessing the efficacy of a treatment for insulin resistance in an individual by monitoring the level of at least one of S2 and S3 in the individual to whom the treatment has been administered.

In another aspect, the invention provides a method for diagnosing insulin resistance or a propensity to insulin resistance in an individual by determining the level of expression of at least one of P20 isoforms S2 and S3 in a cell of an individual, and comparing the level to a reference level characteristic of a cell of the same type in an individual not suffering from insulin resistance or diabetes wherein a level of expression that is higher than the reference level is diagnostic of insulin resistance or a propensity to insulin resistance in the individual. In one embodiment, the levels of both S2 and S3 are determined. In another embodiment, the levels of both S2 and S3 are higher than the reference level. In another embodiment, the level of expression of S2 and/or S3 is the same as or greater than a second reference level, wherein said second reference level is characteristic of an individual with insulin resistance.

In another aspect, the invention provides a method of assessing the efficacy of a treatment for insulin resistance in an individual by monitoring the level of at least one of S2 and S3 in the individual to whom the treatment has been administered.

In another aspect, the invention provides a method of treating insulin resistance in an individual by administering a treatment or an agent that reduces the level of P20 isoforms S2 and S3 in the individual. In one embodiment, the agent is identified by the methods of screening described above.

In another aspect, the invention provides the use of an agent that reduces the level of at least one of S2 and S3 in a cell in the preparation of a medicament for treatment of insulin resistance.

BRIEF DESCRIPTION OF THE DRAWINGS

FIG. 2 shows a two-dimensional phosphoprotein map of insulin-stimulated rat extensor digitorum longus ("EDL") muscle. EDL muscle strips were radiolabelled with $^{32}$P, treated with 50 nM insulin for 30 minutes, then 100 μg protein from each sample was separated by two-dimensional electrophoresis and detected by autoradiography. The denoted proteins were identified either by amino acid sequencing or by western blot analysis. Note that P20(S1) refers to the isoform of P20 with pI value of 6.0. The experiments were performed four times and the figure shown is from one representative experiment.

FIG. 3 shows interplay between insulin and its antagonists on the phosphorylation of P20. $^{32}$P-labelled EDL muscle strips were treated without or with different hormones for 30 min at the following concentrations: insulin, 50 nM; amylin, 50 nM; epinephrine, 50 nM; and calcitonin gene-related peptide ("CGRP"), 50 nM. Phosphorylation of P20 was analysed by two-dimensional gel electrophoresis ("2-DE") and quantitated using phosphorimaging software. The table in the lower panel represents the quantitative data for the three phosphoisoforms of P20. The results are expressed as mean photostimulated luminescence ("PSL") values±S.D. for four independent observations. † shows significant difference (p<0.05) between insulin treated samples and insulin plus amylin treated samples. ‡ shows significant difference (p<0.05) between amylin treated samples and insulin plus amylin treated samples. Note that similar results were observed when adding these agonists sequentially (i.e., pre-incubation with insulin for 15 min, followed by addition of amylin, CGRP or epinephrine for another 15 min, or vice versa).

FIG. 6 shows mRNA abundance and protein concentration of P20 is not altered in rats treated with dexamethasone. Panel I: northern blot analysis. RNA was prepared from the EDL muscles of saline- (A) or dexamethasone-injected rats (B), and also from the EDL muscle strips treated without (C) or with 50 nM amylin (D) for 30 min in vitro, blotted and probed with the labelled P20 cDNA. The negative image of the ethidium bromide-stained RNA loaded in each lane is also shown. Quantitative analysis was performed using a phosphorimager. Panel II: western blot analysis of P20. 30 μg of total proteins from EDL muscles treated as in panel I was separated by 12.5% SDS-PAGE, probed with anti P20 antibody as in FIG. 1. The table in Panel III represents the increased/decreased fold in P20 mRNA and protein level under the respective treatment, relative to saline-treated control rats. The result is expressed as the mean±S.D. from three individual experiments.

FIG. 7 shows the effect of P20 over-expression on glucose uptake in L6 myotubes. A: L6 cells were transfected with pCXN2-GLUT4myc, or pCXN2-GLUT4myc and pcDNA.P20. Following selection with 400 μg/ml G418, clones expressing myc-tagged GLUT4 alone (GLUT4myc) and clones expressing both myc-tagged GLUT4 and P20 (GLUT4myc+P20) were expanded, and differentiated as described in the Methods. 30 μg of cell lysates from L6 myotubes were separated by 10% SDS-PAGE. The levels of P20 and myc-tagged GLUT4 expression were analysed by western blot, using specific anti-p20 and anti-GLUT4 antibodies respectively. B: The cell lines selected in A were differentiated in 6-well plates, and assayed for 2-deoxyglucose uptake in response to insulin or insulin plus amylin as described in the Methods (n=4, expressed as mean±S.D.). Note that the Figure shows the result of a typical experiment, and that similar results were also obtained from at least another two independent transfectants which express myc-tagged GLUT4, or myc-tagged GLUT4 plus P20. * indicates the values that are significantly different (P<0.01) from corresponding values in cells overexpressing GLUT4myc alone.

DETAILED DESCRIPTION OF THE INVENTION

I. General Techniques

The practice of the present invention will employ, unless otherwise indicated, conventional techniques of molecular biology (including recombinant techniques), microbiology, cell biology, biochemistry, nucleic acid chemistry, and immunology, which are within the skill of the art. Such techniques are explained fully in the literature, such as, Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); PCR: The Polymerase Chain Reaction, (Mullis et al., eds., 1994); Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. jointly referred to herein as "Harlow and Lane"), Beaucage et al. eds., Current Protocols in Nucleic Acid Chemistry John Wiley & Sons, Inc., New York, 2000).

II. Introduction

We have recently used comparative proteomic analysis to systematically investigate the phosphorylation cascades evoked by insulin and its antagonists in rat skeletal muscle, and have identified a novel phosphoprotein P20 as the common intracellular target of these hormones (23, 24). Insulin and its antagonistic hormones amylin, epinephrine and calcitonin gene-related peptide (CGRP), through distinctive signaling pathways, phosphorylate P20 at different serine residues to produce multiple phospho-isoforms of this protein. In the Examples, infra, we demonstrate that P20 in skeletal muscle from diabetic rats with insulin resistance has an abnormal phosphorylation pattern, although the expression level of this protein is not changed. Moreover, the responsiveness of P20 to insulin and amylin is also altered in insulin resistant animals.

Our results demonstrate that insulin resistance in skeletal muscle is associated with the appearance of the two P20 phospho-isoforms S2 and S3, and also with the inability of insulin to suppress the amylin-mediated phosphorylation of these two isoforms. Thus, increased phosphorylation of two isoforms of P20, S2 and S3, is associated with insulin resistant states in general. In the absence of hormone stimulation, phosphorylation of S2 and S3 is hardly detected in the non-diabetic cells and animals, e.g., in muscle samples, but two phospho-isoforms are abundant in cells from the insulin resistant animals (e.g., about 5-fold higher than non-insulin resistant animals).

Further, in insulin resistant cells, addition of insulin decreased amylin-induced phosphorylation of S2 and S3 is greatly attenuated compared to normal (non insulin resistant) cells or animals.

As used herein, "P20" means the protein cloned by Inayuma, Y. et al Gene 178(1–2):145–50 (1996) and its homologs in mammalian species. See also Wang et al., 1999, FEBS Lett 457:49–52, and Wang et al., 1999, FEBS Lett 462:25–30, 1999. P20 exists in three phosphorylated isoelectric variants, referred to as S1, S2 and S3. In rats, S1 (pI=6.0) is phosphorylated at serine 157; S2 (pI=5.9) is phosphorylated at serine 16, and S3 (pI=5.6) is phosphorylated at multiple sites, including serine 16. Homologues of S2 and S3 have been identified in human skeletal muscle by Western blotting and two dimensional electrophoresis equivalent to the methods employed to identify these phosphoisoforms in rodent tissues. Homologues in other mammals can be characterized using methods described herein.

III. Drug Screening Methods

Phosphoprotein P20 and its isoforms or isovariants (e.g., phosphoisoform S1, S2, or S3) can be targets for drug screening purposes. Accordingly, methods of screening compounds that are potential drugs are provided (e.g., methods for screening for an agent useful for treatment of insulin resistance or syndrome X-associated conditions). In one embodiment, the methods of identifying compounds that are potential drugs that interact with and/or bind to a phosphoprotein P20 and its isoforms (e.g., S1, S2 and/or S3 isoforms) are provided. In a related aspect, the invention provides methods of screening for drugs which interact with and/or bind to a protein or receptor associated with P20 or its isoforms (e.g., glucose transporters) are provided.

Preliminary screens can be conducted by screening for compounds capable of binding to P20, as at least some of the compounds so identified are likely modulators of P20 phosphorylation at the S2 and S3 sites. Binding can be detected using standard techniques, such as assays including, but not limited to, methods that measure co-precipitation, co-migration on non-denaturing SDS-polyacrylamide gels, and co-migration on Western blots. The P20 protein utilized in such assays can be naturally expressed, cloned or synthesized. The binding can be assessed using purified P20, cell-free systems, or intact cells (e.g., recombinant cells expressing P20). In assays, the P20 and/or putative drugs may be labeled with a detectable marker (e.g., radiolabel or a non-isotopic label such as biotin or fluorescent marker). Drug candidates can be identified by choosing compounds which bind with affinity, preferably high affinity, to the phosphoprotein P20 and its isoforms expressed in the cell, using techniques well known in the art. Drug candidates can also be screened for selectivity by identifying compounds that bind to phosphoprotein P20 and its isoforms but do not bind to any other receptors or receptor sites. In another embodiment, drug candidates are screened to identify compounds that bind to a protein associated with P20 or its isoforms (e.g., glucose transporter or receptor) and exert its effects. Accordingly, a method of drug screening involves exposing mammalian cells expressing P20 or its isoforms to one or a plurality of drugs, then determining those drugs which bind to the phosphoprotein P20 and its isoforms expressed in the mammalian cell, and thereby identifying drugs which interact with and/or bind to the phosphoprotein P20 and its isoforms. Compounds that bind to P20 or P20-associated proteins can be subjected to additional assays to determine their therapeutic activity. Preferred compounds are those that bind P20 and modulate phosphorylation of S2 and/or S3.

Figure 7:
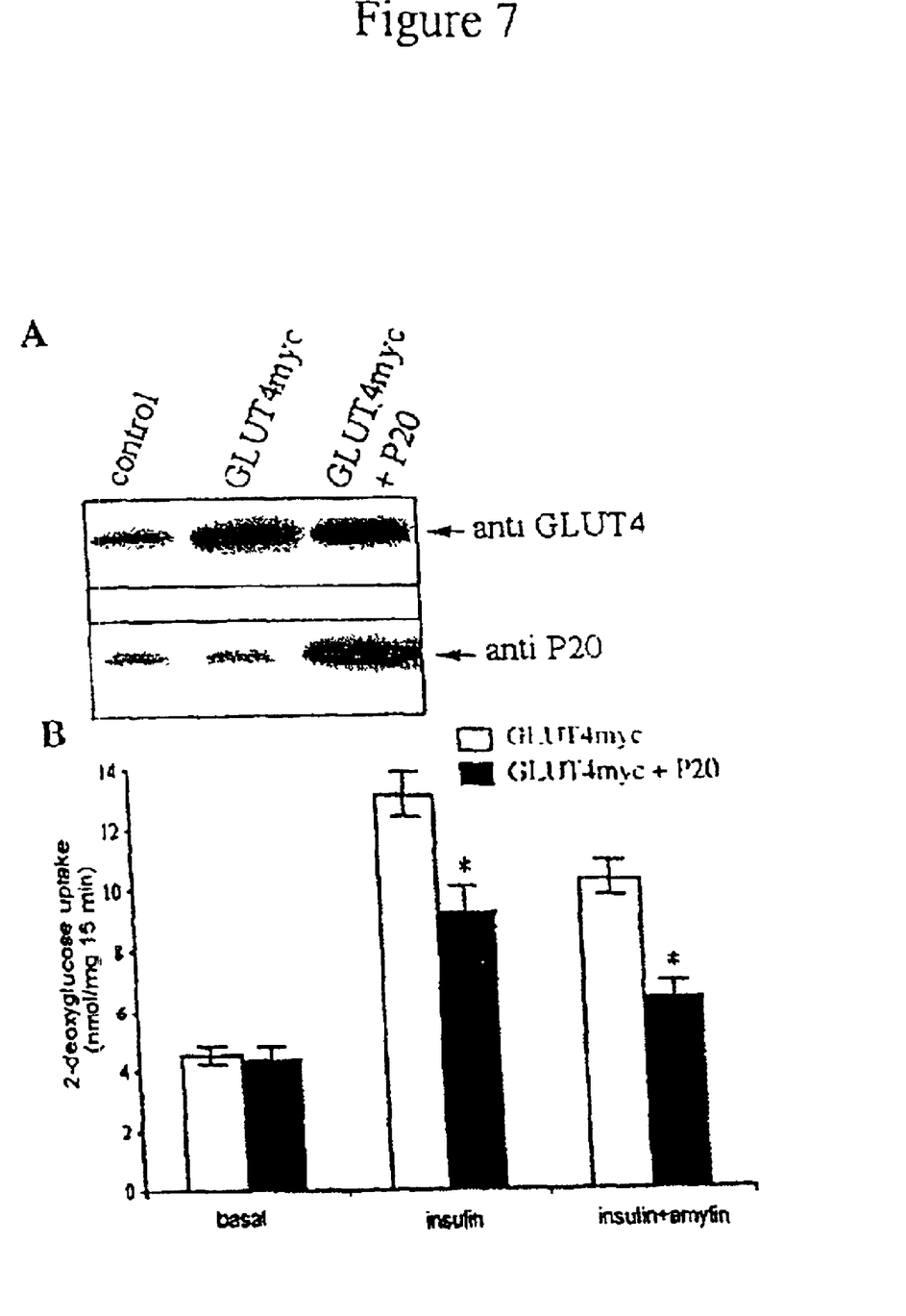

One method that can be used for drug screening involves using mammalian cell(s) that express P20 (or its isoforms), contacting the cells with one or more test compounds, and monitoring the effect of the compound(s) on the cells. One such effect that can be monitored or measured is the uptake of glucose or a variant of glucose (e.g., uptake of 2-deoxyglucose, as shown in FIG. 7). Another effect that can be monitored is the phosphorylation of P20 and/or the generation of isoforms such as S1, S2, and/or S3. Phosphorylation patterns can be assessed by methods known in the art and by those assays described herein.

In one aspect, the invention provides a method for identifying an agent useful for treatment of insulin resistance by contacting a mammalian cell that expresses P20 with a test agent and determining if the agent suppresses the level of at least one of P20 isoforms S2 and S3 (e.g., compared to expression in the absence of the test agent). Suppression of levels of S2 and/or S3 by an agent is indicative that the agent is useful for treatment of insulin resistance and related conditions (e.g., syndrome X-related). Suppression means a lower or reduced level of S2 and/or S3 compared to a cell of the same cell type not contacted with the test agent. Preferably a test compound useful for treatment of insulin resistance is one that reduces the levels of S2 and/or S3 by at least about 20%, often by at least about 40%, very often by at least about 50%, and sometimes by at least about 60% compared to a control cell.

In certain embodiments, the mammalian cell is rodent (e.g., rat, mouse, hamster or the like) or primate (e.g., human or non-human primate). The mammalian cell can be an isolated cell or cells (e.g., in in vitro cell culture), a cell in a tissue (e.g., a biopsy tissue), a cell in a test animal or any other cell. For example, the cell can be a myocyte, a muscle cell (e.g., skeletal muscle, soleus muscle, extensor digitorum longus muscle, heart muscle, or smooth muscle), an adipocyte, or a blood cell. Thus, for example, isolated tissues, such as isolated skeletal muscle tissue can be used (e.g., as is described in the Examples). An example of a suitable mammalian cell type is L6 cells, as used in the experiment depicted by FIG. 7.

Cells expressing P20 can be cells that naturally express this protein. Alternatively, they can be recombinant cells. Phosphoprotein P20 (e.g., P20 isoforms) can be expressed in mammalian cells by using a plasmid or expression vector which comprises a genetic sequence (e.g., DNA sequence) which encodes for phosphoprotein P20 (e.g., P20 isoforms).

In an embodiment, the cell is an insulin resistant cell. By "insulin resistant" is meant a cell that demonstrates a subnormal dose-response when treated with insulin, in an insulin-responsive process or pathway or, for example, in the activation or inhibition of an insulin-responsive enzyme and/or is a cell or tissue isolated from an animal that is insulin resistant. Animals that are insulin resistant include, but are not limited to, a human diagnosed with insulin resistance or type II diabetes, animals that are genetically insulin resistant (e.g., ob/ob mice), or animals in which insulin resistance or diabetes has been experimentally induced (e.g., by administration of dexamethasone, maintenance on a high fat diet, etc.).

Insulin resistance of ex vivo cultured cells or tissues can be generated by treatment with amylin, but this is not the only way to achieve such preparations. Other molecules that can generate insulin resistance following in vitro treatment of cells or tissues with them, include CGRP1 or CGRP2; epinephrine; or norepinephrine. In addition, insulin-resistant cells or tissues may be generated by first treating an animal, such as a rodent, with other hormones that are capable of generating insulin resistance only in vivo and not directly in vitro. Examples in this second category of hormones include glucocorticoid agonists (e.g., cortisol, corticosterone, prednisone or dexamethasone) and other hormones (e.g., growth hormone and growth hormone agonists); hormones in both these classes can evoke insulin resistance in vivo. Ex vivo cultures of cells or tissues, such as liver, adipose tissue, skeletal muscle or cardiac muscle, are then prepared from animals made insulin resistant by treatment with these hormones, and are employed in the assays. Cells or tissues generated from animals with genetically based insulin resistance and obesity can also be employed in assays. Examples of useful rodent strains are: ob/ob mice, db/db mice, fa/fa rats and LAN-cp rats. Further sources of cells or tissues that can be usefully employed in such assays are those derived from animals made insulin resistant by nutritional manipulations or from insulin resistant humans. Examples of useful nutritional manipulations for rodents include feeding to otherwise normal rodents of diets that contain supraphysiological amounts of fat or infraphysiological amounts of protein. Insulin resistant cells or cell lines also can be obtained from the American Type Culture Collection (ATCC, P.O. Box 1549 Manassas, Va. 20108). Insulin resistance of a cell (line) or animal can be determined either in vitro or in vivo using routine methods. For example, in vitro testing can involve incubating mammalian cells with and without insulin and then determining the effect of insulin on glycogen synthesis and/or glucose uptake. In vivo testing can involve administering insulin to a mammal in a fasting glucose test and then measuring glycogen synthesis and/or glucose uptake. In humans, insulin resistance can be assessed by any of a variety of methods known in the art (see, e.g., Bergman et al., 1985, *Endocrine Review* 6:45–86; Reaven et al., 1979, *Diabetologia* 16:17–24).

As noted, suppression of levels of S2 and/or S3 by an agent is indicative that the agent useful for treatment of insulin resistance and related conditions (e.g., syndrome X-related conditions). Levels (sometimes referred to as "expression levels") of S2 and/or S3 in a cell can be determined by any number of methods including, but not limited to, two-dimensional gel electrophoresis, chromatographic methods (e.g., HPLC), immunological methods (e.g., immunoprecipitation using antibodies specific for S2 or S3, radioimmune assays (RIA), Western blotting, etc.), and the like, including use of various imaging and analytical methods for quantification of levels of specific proteins (e.g., specific phosphorylated proteins). Conveniently, phosphorylation of P20 in cells can be monitored using radioisotopes of phosphorous, for example as described in the Examples, infra.

The invention further provides a method for screening for an agent useful for treatment of insulin resistance by contacting a mammalian cell expressing P20 and an agent, determining an expression level of at least one of P20 isoforms S2 and S3; and comparing the level of at least one of P20 isoforms S2 and S3 to a reference level. In embodiments, the reference expression level is characteristic of (i) expression in a similar cell not exposed to the agent or (ii) expression in a cell that is not insulin resistant. An agent is potentially useful for treatment of insulin resistance when the expression level in the presence of the agent is lower than (i) or similar to (ii). In this context, "lower than" means an expression level of S2 and/or S3 at least about 20%, lower than (i), often at least about 40%, often at least about 50%, and sometimes at least about 60%. In this context, "similar" means an expression level that is within 2-fold of (ii), preferably within 1.5-fold of (ii).

As discussed in the Examples, amylin and insulin have countervailing effects on the levels of S2 and S3. Amylin (as well as agents such as CGRP1, CGRP2, epinephrine or norepinephrine) can be used to induce phosphorylation of P20 during, prior to, or after contacting the cell and the test agent. Insulin (or other insulin agonist) can be contacted with the cells to measure the insulin dose-response of one or more processes in the tissue (and hence the insulin responsiveness of the cell or tissue). Thus, treatment with an insulin agonist and measurement of an indicator variable is the probe capable of demonstrating insulin resistance in the cell or tissue.

Insulin resistance in skeletal muscle is associated with the appearance of the two P20 phospho-isoforms S2 and S3, and with the inability of insulin to suppress the amylin-mediated phosphorylation of these two isoforms. In one aspect of the invention, a test agent is assayed for the ability to restore the ability of insulin to suppress the phosphorylation of S2 and S3.

It will be appreciated that the screening assays of the invention can be carried out in the presence of insulin (or an insulin substitute, such as an insulin receptor agonist). Thus, in one embodiment, the screening assay is carried out in the presence of insulin and/or the cell is exposed to insulin or insulin analog at the time of, prior to, or after the contacting with the test compound. The insulin can be natural, synthetic, recombinant, primate (e.g., human), or rodent (e.g., rat or mouse). Examples of insulin agonists include, without limitation, any structure of insulin in which one or more amino acid residues are substituted to yield an altered molecule with insulin-like activity (e.g., insulin-like dose-response relationships in vivo or in vitro). Examples of insulin agonists that can be employed in such assays include: human insulin; [LysPro]human insulin (a synthetic analog of human insulin), and rat insulin I or rat insulin II, which are naturally occurring homologues of human insulin. The amount of insulin used is usually within the range 1 pM to 1 $\mu$M, often 30 nM to 100 nM (e.g., 50 nM), i.e., a range that spans the concentration-response of a tissue process or pathway that is informative concerning the relative insulin sensitivity of the tissue. Examples of such processes include glucose transport or incorporation of glucose into glycogen, which are informative in skeletal muscle; or suppression of basal or glucagon-stimulated glucose output from hepatocytes or the isolated perfused liver, which inform on liver function. In insulin resistant or diabetic animals or tissues, amylin-evoked phosphorylation of S2 and S3 is not greatly decreased by the administration of insulin, while in normal animals or tissues, insulin significantly decreases phosphorylation of S2 and S3 (e.g., typically by at least about 30%, more often by at least about 50%). The contacting of cells and insulin can be in vivo or in vitro.

In another embodiment, at the time of, prior to, or after the contacting with the test compound, the cells (e.g., tissues) used in the screening assay are exposed to an agent that induces phosphorylation of S2 and/or S3. Exemplary agents are hormones such as amylin, CGRP1, CGRP2, epinephrine or norepinephrine (including analogs of each). The hormone, e.g., amylin, can be natural, synthetic, recombinant, primate (e.g., human), or rodent (e.g., rat or mouse). The amount of hormone administered is an amount sufficient to induce insulin resistance in an informative pathway or process, such as glucose transport or incorporation of glucose into glycogen, which are informative in skeletal muscle, for example (for amylin) about 10 nM to 100 nM (e.g., 50 nM). The contacting of cells and hormone can be in vivo or in vitro.

Compounds or agents which are contemplated as potential drugs include, but are not limited to, antibodies (polyclonal, monoclonal, recombinant, chimeric, etc.), synthetic molecules, small molecules (e.g., small organic molecules), peptides, compounds comprised of nucleic acids, and proteins. One source of potential drugs are libraries of natural or synthetic compounds. The creation and simultaneous screening of large libraries of synthetic molecules can be carried out using well-known techniques in combinatorial chemistry, for example, see van Breemen (1997) *Anal Chem* 69:2159–64; Lam (1997) *Anticancer Drug Des* 12:145167 (1997); Gold (1995) *J. Biol. Chem.* 270:13581–13584). In addition, a large number of potentially useful activity-modifying compounds can be screened in extracts from natural products as a source material. Sources of such extracts can be from a large number of species of fungi, actinomyces, algae, insects, protozoa, plants, and bacteria. Those extracts showing activity can then be analyzed to isolate the active molecule. See for example, Turner (1996) *J. Ethnopharmacol* 51(13):3943; Suh (1995) *Anticancer Res.* 15:233239. Several methods of automating assays have been developed in recent years so as to permit screening of tens of thousands of compounds in a short period. See, e.g., Fodor et al., 1991, Science 251:767–73, and other descriptions of chemical diversity libraries, which describe means for testing of binding affinity by a plurality of compounds.

IV. Diagnostic Methods

The invention provides a method for diagnosing insulin resistance in an individual by determining the level of expression of at least one of P20 isoforms S2 and S3 in a cell of an individual, and comparing the level to a reference level characteristic of a cell of the same type of an individual or population of individuals (i) not suffering from insulin resistance or diabetes or (ii) diagnosed with insulin resistance or diabetes. As used herein, the term "individual" includes mammals such as humans, non-human primates, commercially valuable animals, pets, and experimental animals (e.g., rodents including mice and rats). Conveniently the method can be carried out by obtaining a biological sample from the individual containing at least one, and preferably many, P20-expressing cells. Examples of such cells include myocytes, muscle cells (e.g., skeletal muscle, soleus muscle, extensor digitorum longus muscle, heart muscle, or smooth muscle), blood cells, and adipocytes. Biological samples can be in the form of tissues (including tissues obtained by biopsy) or tissue cultures or cells derived therefrom, and the progeny thereof, cells from blood, whole cells, cell fractions, cell extracts, and cultured cells or cell lines), body fluids (e.g., urine, sputum, amniotic fluid, synovial fluid), or from media (from cultured cells or cell lines), and the like. Biological samples also include cells manipulated after removal from the individual, e.g., by exposure to insulin, amylin, CGRP or epinephrine, or enrichment for specific cell types (e.g., myocytes or adipocytes).

In one embodiment, the reference level is a level of expression characteristic of a cell of the same type in an individual or population of individuals not suffering from insulin resistance or diabetes. In another embodiment the reference level is a level of expression characteristic of a cell of the same type in an individual or population of individuals diagnosed with insulin resistance or diabetes. In one embodiment, either one of S2 and S3 levels are determined. In another embodiment, the levels of both S2 and S3 are determined. In one embodiment, a diagnosis of insulin resistance is made when the levels of S2 and/or S3 are higher (e.g., statistically significantly higher) than the level characteristic of an individual not suffering from insulin resistance or diabetes and/or lower (e.g., statistically significantly lower) than the level characteristic of an individual diagnosed with insulin resistance or diabetes.

In some cases, it will be desirable to establish normal or baseline values (or ranges) for S2 and/or S3 levels. Normal (e.g., low) levels can be determined for any particular population, subpopulation, or group of organisms according to standard methods well known to those of skill in the art. Generally, baseline (normal) levels of S2 and/or S3 for healthy individuals are determined by quantitating the levels in biological samples obtained from normal (healthy) subjects not suffering from insulin resistance or diabetes. For certain samples and purposes, one may desire to quantitate the amount of S2 and/or S3 with reference to the total amount of P20 protein in the sample, and/or on a per cell basis. To determine the cellularity of a sample, one may measure the level of a constitutively expressed gene product or other gene product expressed at known levels in cells of the type from which the sample was taken. It is possible that normal (baseline) values may differ somewhat between different cell types or according to the age, sex, or physical condition (other than presence of insulin resistance) of a patient. Thus, for example, when an assay is used to determine changes in S2 and/or S3 levels associated with insulin resistance, the cells used to determine the normal range of expression can be cells from persons of the same or a different age, depending on the nature of the inquiry. Application of standard statistical methods permits determination of baseline levels of expression, as well as permits identification of significant deviations from such baseline levels. It will be appreciated that the assay methods do not necessarily require measurement of absolute values of S2 and/or S3, unless it is so desired, because relative values are sufficient for many applications of the methods of the present invention.

In a different embodiment, the invention provides a method of assessing the efficacy of a treatment for insulin resistance. The assays of the invention may also be used to evaluate the efficacy of a particular therapeutic treatment regime in animal studies, in clinical trials, or in monitoring the treatment of an individual patient. In these cases, it may be desirable to establish the baseline for the patient prior to commencing therapy and to repeat the assays one or more times through the course of treatment, usually on a regular basis, to evaluate whether S2 and/or S3 levels are moving toward the desired endpoint (e.g., reduced expression of S2 and/or S3) as a result of the treatment.

V. Treatment Methods

Without intending to be bound by any particular mechanism, as noted in the Examples, infra, increased phosphorylation of S2 and S3 characteristic of insulin resistance is not due to the increased expression of P20, but likely due to a defect in the intracellular signal transduction pathways that lead to generation of its phosphorylated isoforms. These results suggest that alterations in phosphorylation of P20 contribute to the development of insulin resistance. Compositions and therapies that reduce the levels of P20 isoforms S2 and/or S2 in an individual are thus useful for the treatment of insulin resistance and related conditions. In accordance with this, the invention provides methods for treating insulin resistance in individuals by administering a treatment (e.g., compound) that reduces the level of P20 isoforms S2 and/or S3 in at least one cell in the individual. As used herein, "treatment" is an approach for obtaining beneficial or desired results including and preferably clinical results. The beneficial or clinical results include but are not limited to an improvement in an individual's ability to be sensitized to insulin and a decrease in an individual's insulin resistance. A treatment plan may occur over a period of time and may involve multiple dosages, multiple administrations, and/or different routes of administration of a therapeutic agent.

In one embodiment, the agent is identified by the methods of screening disclosed herein. The treatment or agent can be administered as a pharmaceutical composition. The pharmaceutical composition can include a drug identified by the method described above and a pharmaceutically acceptable carrier. In some embodiments, the pharmaceutical compositions of the invention are formulated for administration by injection (e.g., intraperitoneally, intravenously, subcutaneously, intramuscularly, etc.). As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. Excipients as well as formulations for parenteral and nonparenteral drug delivery are set forth in Remington's Pharmaceutical Sciences 19th Ed. Mack Publishing (1995). Once the candidate drug has been shown to be adequately bio-available following a particular route of administration, for example orally or by injection and has been shown to be non-toxic and therapeutically effective in appropriate disease models, the drug may be administered to patients by that route of administration determined to make the drug bio-available, in an appropriate solid or solution formulation, to gain the desired therapeutic benefit.

EXAMPLES

Example 1

Materials and Methods

Male Wistar rats were fed standard rat chow (NRM Diet 88, Auckland, New Zealand) with water ad libitum. [$^{32}$P]-orthophosphate and [$^{14}$C(U)]-D-glucose were purchased from ICN. 2-deoxy-D-[$^{3}$H] glucose (1 mCi/ml) was from NEN and iodine-125 from Amersham pharmacia. Human insulin was Actrapid from Novo Nordisk. Rat amylin and CGRP were purchased from Bachem (Torrance, Calif.); epinephrine was from David Bull Laboratories; and dexamethasone from Sigma. The two-dimensional gel electrophoresis (2-DE) system and reagents were from Pharmacia. Anti-P20 polyclonal antibody was a generous gift from Dr. Kanefusa Kato (25). Anti-GLUT4 (H-61) was from Santa Cruz. The enhanced chemiluminescence (ECL) detection system was from Boehringer. The total cellular RNA extraction reagent (TRIZOL®), G418, Lipofectamine Plus reagent and random priming labelling kits were from Life Technology. pCXN2-GLUT4myc, which expresses myc-tagged GLUT4 in mammalian cells, was kindly provided by Dr David James (The University of Queensland, Australia).

Establishment of the Dexamethasone- or High Fat-induced Rat Models with Insulin resistance All experimental protocols were approved by the Institutional Animal Ethics Committee. Male Wistar rats were injected with dexamethasone (3.1 mg/kg/day, intraperitoneally) for 7 days. The daily weights of rats in both control and dexamethasone-treated groups were monitored. By the end of the treatment period, the mean weight of the control group had increased by 12±1%, whereas that of the glucocorticoid-treated group had sharply decreased, by 16±2% (n=3 experiments, each with 3 rats per group). Rats were fasted for 18 h prior to each experiment and were killed by cervical dislocation. Blood was obtained by cardiac puncture from anesthetized animals. The mean blood glucose concentration was 5.4±0.2 mM and 10.8±0.6 mM in control and dexamethasone-treated rats, respectively, as measured with a YSI 2300STAT glucose/lactate analyser (Yellow Springs Instruments). The insulin resistant state of the skeletal muscle was further confirmed using an in vitro [$^{14}$C(U)]-D-glucose incorporation assay, which demonstrated over 95% reduction in the rates of insulin-stimulated glycogen synthesis in dexamethasone-treated rats (results not shown). Insulin and amylin concentrations in the blood of normal and insulin resistant rats were determined as described (17). Rats with insulin resistance induced by chronic high fat feeding were generated as described previously (26).

Dissection and Metabolic Radiolabelling of Rat Skeletal Muscle Strips

Rat extensor digitorum longus (EDL) muscle strips were prepared from 18 h-fasted rats. Dissection and isolation of muscles were carried out under anaesthesia with pentobarbital (5–7 mg/100 g of body weight, intraperitoneally) as described previously (23). Each muscle was split into three ~1 mm width strips. Muscle strips were pre-incubated in a shaking incubator at 30° C. for 1 h in 5 ml of Dulbecco's Modified Eagle's medium without sodium phosphate. All incubation media were gassed with a mixture of 95% $O_2$ and 5% $CO_2$. The muscle strips were subsequently transferred to similar flasks containing identical medium plus 0.25 mCi/ml [$^{32}$P]-orthophosphate and incubated for a further 4 h to equilibrate the internal ATP pool (23, 24). Human insulin, rat amylin, epinephrine or CGRP were then added to the incubation media for 30 min at stated final concentrations. Reactions were terminated by freezing muscle strips in liquid nitrogen immediately after incubation. Muscle strips were then weighed and stored at −80° C. until further analysis.

Muscle Extraction and Two-dimensional Gel Electrophoresis (2-DE)

Muscle strips were homogenized in 2-DE lysis buffer (9M urea, 2% v/v triton X-100, 2% v/v pharmalyte pH 3–10, 200 mM DTT, 8 mM PMSF) for 5 min on ice. The lysates were briefly sonicated and microcentrifuged at 12,000 rpm for 10 min to remove debris. Protein concentrations were determined by the Bradford method and radioactivity was measured by liquid scintillation counting. $^{32}$P-labelled lysates with equivalent amounts of radioactivity were isoelectrically focused on IPG Drystrip pH 4–7 and pH 3–10 Linear gels using a multiphor RII electrophoresis system according to the manufacturer's instructions. Second dimensional SDS-PAGE was carried out using ExcelGel™ precast 12–14% acrylamide gradient gels. After electrophoresis the gels were fixed in 10% glacial acetic acid, 40% ethanol and the proteins visualized by phosphorimaging or autoradiography. In all figures, the gels are displayed with the acidic end of the isoelectric focusing dimension to the right and the direction of SDS-PAGE from top to bottom.

cDNA Cloning, Construction of Expression Vector and Transfection.

A full length cDNA encoding wild type rat P20 was cloned by RT-PCR, using a forward primer 5'GCCCGCG-GATCCATGGAGATCCGGGTGCCTGTG3' (SEQ ID NO: 1) and reverse primer 5'GCCCGGGATCCCTACTTG-GCAGCAGGTGGTGAC3' (SEQ ID NO: 2) respectively. The resulting clone was validated by DNA sequencing, and then inserted into the multiple cloning site of cytomegalovirus promoter-driven eukaryotic expression vector pcDNA3.1 (referred to as pcDNA.P20).

L6 myoblast cells were transfected with pCXN2-GLUT4myc (27), or co-transfected with pCXN2-GLUT4myc and pcDNA.P20, using Lipofectamine Plus reagent according to the manufacturer's instructions. Stable transfectants were selected in medium containing the neomycin analogue G418 at 400 μg/ml. At 10 days after transfection, the clones were selected using sterilised steel rings and expanded separately in the presence of G418. Clones that express P20 and myc-tagged GLUT4 were chosen by western blotting and used for further experiments.

Western Blotting

About 50 μg proteins from liver, heart, epididymal fat pad, aortic smooth muscle, EDL muscle, soleus muscle tissues and whole blood obtained from 18 h-fasted male Wistar rats were separated by SDS-PAGE and subsequently transferred to nitrocellulose membranes. The membranes were blocked over night at 4° C. and then incubated with rabbit anti-P20 polyclonal antibody (1:1000) for 2 h at room temperature. After incubation with streptavidin-biotinylated horseradish peroxidase-conjugated secondary antibody for another 1 h at room temperature, the proteins immunoreactive to the primary antibody were visualised by enhanced chemiluminescence (ECL) detection according to the manufacturer's instructions.

Northern Blot Analysis

Total cellular RNA was isolated from EDL muscle of 18 h-fasted control and dexamethasone-treated rats using TRI-ZOL reagent. 15 μg of RNA from each sample was separated by 1.5% agarose-formaldehyde gel electrophoresis and subsequently transferred to Hybond-N$^+$ nylon membranes by capillary blotting in 20×SSC. The P20 cDNA probe was labelled with $^{32}$P-dCTP using a random primer labelling system. The membranes were pre-incubated with hybridisation buffer (0.5 M $Na_2HPO_4$, pH 7.2, 10 mM EDTA, 7% SDS) for 3 h at 65° C. and subsequently incubated with fresh buffer containing the labelled probe for 18 h. Membranes were then washed, analysed using a phosphorimager and quantitated by MacBAS v2.5 software. For comparison, RNA samples from EDL muscle strips treated with or without 50 nM amylin were also analysed in parallel.

Glucose Uptake Assays

L6 cells stably overexpressing myc-tagged GLUT4, or myc-tagged GLUT4 plus P20, were grown in 6-well plates and differentiated into myotubes in DMEM containing 2% fetal bovine serum for 7 days. The cells were deprived of serum for 16 h prior to experiments. For glucose uptake assays, L6 myotubes were rinsed three times with Krebs-Henseleit buffer (KHB) and incubated in KHB with or without hormones (insulin or insulin plus amylin) at the indicated concentrations for 15 min at 37° C. Carrier-mediated glucose uptake of 10 μM 2-deoxy-D-[$^3$H] glucose in the above solution was measured for 15 min at 37° C. This was followed by rinsing the cells three times with ice-cold PBS and cell disruption with 0.1 N NaOH. The associated radioactivity was determined by liquid scintillation counting. The protein concentration was measured with a BCA protein quantitation kit (PIERCE). The nonspecific uptake was determined in the presence of 10 μM cytochalasin B and subtracted from each value.

Data Analysis

Autoradiography films were scanned and digitised using a Sharp JX-325 scanner, and protein spots detected, quantitated and analysed using the Melanie II software package, ver. 2.2 (Biorad). The detection parameters were: smooth 2, Laplacian threshold 3, partials threshold 1, saturation 90, peakedness increase 100 and minimum perimeter 10. The matching of multiple features to one feature was not allowed. The pixel value is the optical density (OD). Features were calculated as a percentage of the sum of VOL (the feature's volume, i.e., the integration of OD over the feature's area) for all features on the gel. The radioactivity of protein spots was also detected by a phosphorimager and analysed by MacBAS v2.5 software. The radiation dose of each spot was displayed in terms of units of photostimulated luminescence (PSL). All the results presented are based on at least three independent experiments. Statistical analysis was performed using the t-test (paired two sample).

Example 2

P20 is the Major Insulin Responsive Phosphoprotein in Rat EDL Muscle Detected By 2-DE P20 was initially isolated from rat skeletal muscle as a by-product during the purification of small heat shock proteins HSP27/28 and αB-crystallin (25). Under normal physiological conditions, it exists as large aggregates. P20 has been thought to be a heat-shock related protein, since it has significant amino acid sequence similarity with αB-crystallin (47%) and HSP27/28 (35%) (25, 28). However, unlike other small HSPs, heat treatment or chemical stress does not induce the expression of P20. Several recent studies suggest that P20 may be an actin-binding protein that is involved in cyclic nucleotide-mediated vasodilation and relaxation of rat smooth muscle, or histamine- and phorbol ester-induced contraction of bovine carotid artery smooth muscle (29–31). Interestingly, this protein is also present at high concentration in circulating whole blood in patients with vascular diseases. It can strongly suppress platelet aggregation in vitro and ex vivo, possibly by inhibiting receptor-mediated calcium influx in platelets (32). However, the precise physiological functions of P20 are still uncertain.

Figure 1:
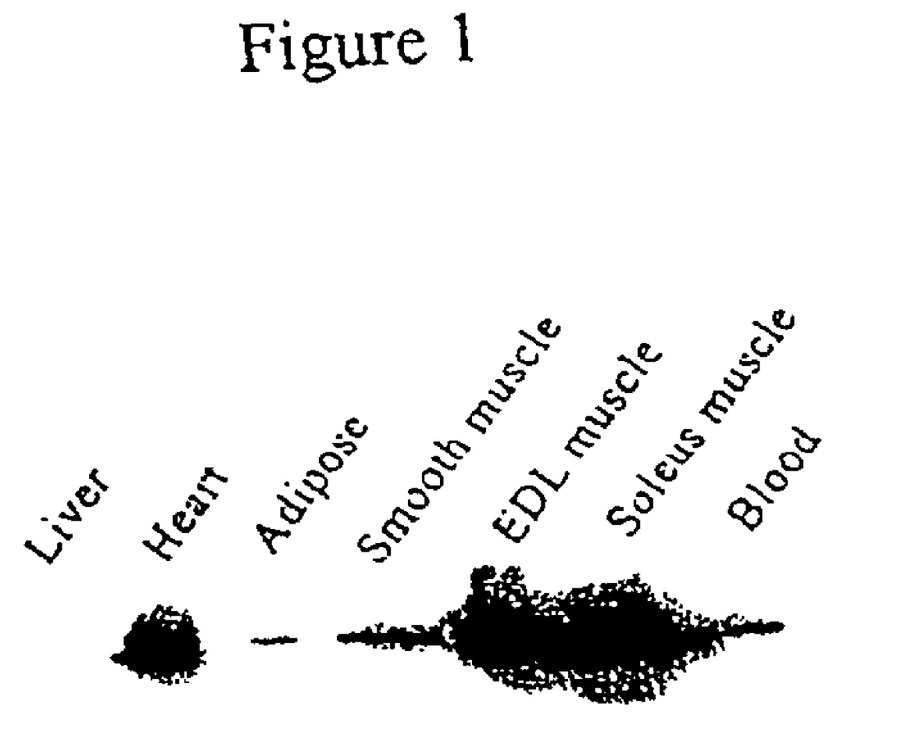
FIG. 1 shows immunoblotting analysis of P20 expression in several different rat tissues. 50 μg of protein from each of the indicated rat tissues was separated by 12.5% SDS-PAGE, and immunoblotted to detect P20 as described in the Examples. The result is the typical representation of three independent observations.
Figure 2:
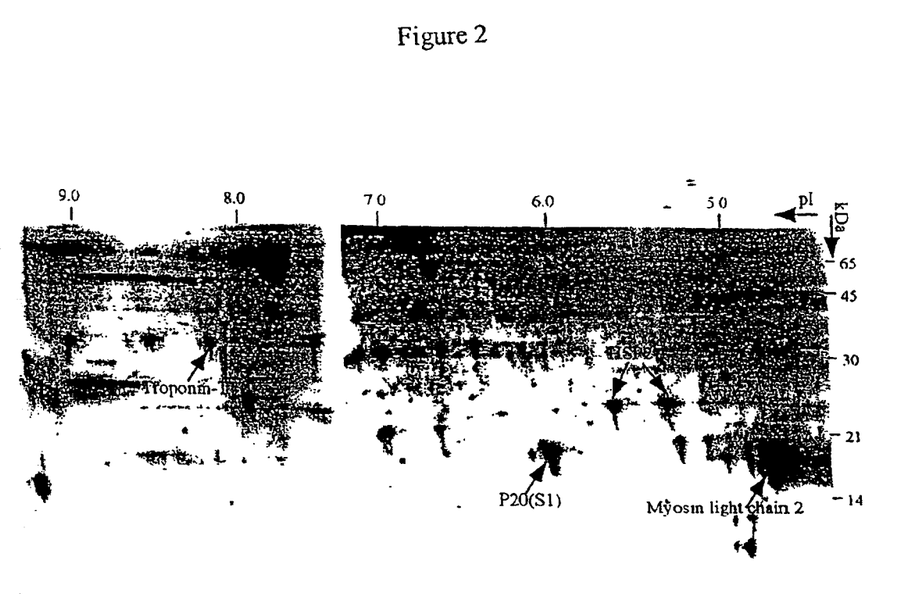

Analysis of the protein content of P20 by western blot showed that this protein is mainly expressed in rat soleus muscle, EDL muscle and heart muscle tissues, which account for 35.1±3.2%, 29.6±2.7% and 23.3±2.5% of the total P20 in all the tested tissues respectively (n=3, expressed as mean±S.D.) (FIG. 1). A small amount of this protein was also detected in smooth muscle (4.9±0.6%) adipose tissue (1.9±0.3%) and blood (5.2±0.6 %). 2-DE analysis of $^{32}$P-radiolabelled rat EDL muscle revealed about 150 phosphoproteins labeled following insulin stimulation (FIG. 2). Quantitative analysis by Melanie II software revealed that P20 is the second most abundant phosphoprotein in insulin-stimulated rat EDL muscle, representing over 2% of the total VOL for all features detected. Moreover, P20 is the only detected phosphoprotein that is responsive to both insulin and its antagonists, as analysed by the proteome approach.

Example 3

Interplay Between Insulin And Amylin On Phosphorylation Of P20

Our previous studies demonstrated that insulin and its antagonists, epinephrine, amylin and CGRP, elicit differential phosphorylation on different sites of P20, thus producing three phosphorylated isoelectric variants of P20 (termed as S1, with a pI value of 6.0; S2, with a pI value of 5.9; and S3, with a pI value of 5.6) (23, 24). Phosphorylation of S1 occurs at serine 157 of P20, and insulin can increase its phosphorylation through a PI-3 kinase mediated pathway. Amylin, CGRP and epinephrine evoke phosphorylation at Ser16 of P20, through a cAMP mediated pathway, leading to the production of the phosphoisoform S2. In addition, these catabolic hormones also induce the phosphorylation of P20 at another two unidentified sites to produce the phosphoisoform S3.

Figure 3:
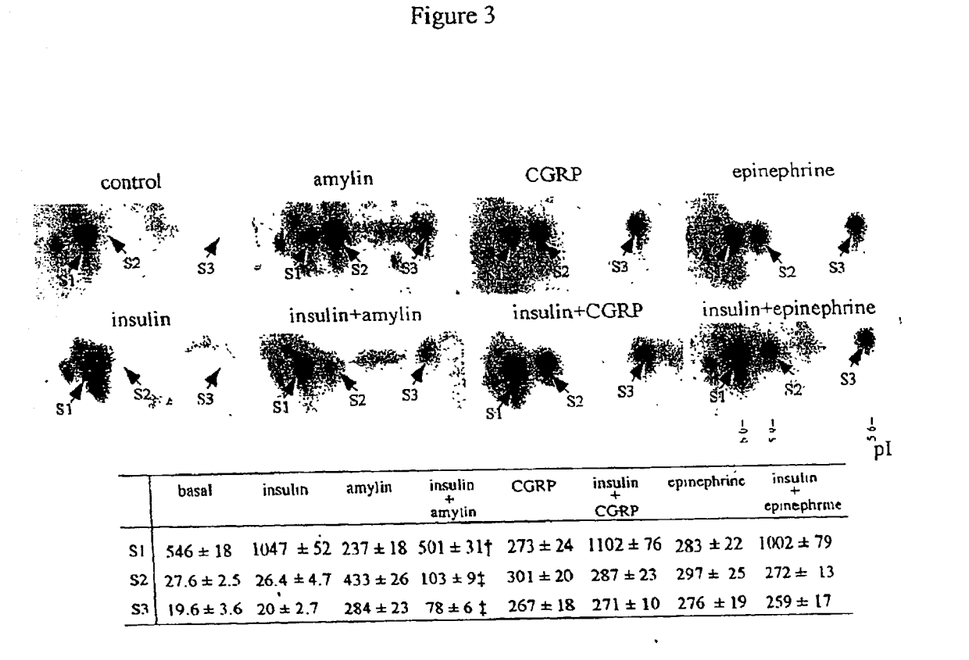

Here, we further investigated the interplay between insulin and several of its antagonists on phosphorylation of P20. Interestingly, we found that insulin and amylin can antagonise each other's actions on the phosphorylation of this protein (FIG. 3). On the one hand, insulin-induced phosphorylation of S 1 was significantly decreased in the presence of amylin. Phosphorylation of S1 in samples treated with 50 nM insulin plus 50 nM amylin was 49% lower than that in samples stimulated with 50 nM insulin alone. On the other hand, insulin blocked amylin-evoked phosphorylation of S2 and S3. In the presence of insulin, phosphorylation of S2 and S3 was decreased by about 72% and 74% respectively, relative to that in muscles treated with amylin alone. However, insulin had no effect on phosphorylation of S2 and S3 induced by the other two catabolic hormones epinephrine and CGRP, and vice versa. This result indicates that "cross-talk" occurs only between the insulin- and amylin-evoked signalling pathways; although all three catabolic hormones are thought to act through G-protein coupled receptors and to have similar metabolic effects. Amylin inhibits the insulin-evoked PI-3 kinase cascade-mediated phosphorylation of S1. Conversely, insulin suppresses the amylin-evoked cAMP pathway-mediated phosphorylation of S2 and S3. Such an inhibitory effect of insulin on amylin's biological actions could provide a reasonable explanation as to why administration of exogenous amylin in physiological quantities did not induce hyperglycemia and insulin resistance in some experimental systems.

The fact that insulin has separate effects on inhibition of biological actions of amylin and CGRP further excludes the possibility that amylin acts solely through a CGRP receptor, although the two peptide hormones are members of the calcitonin related polypeptide family (33). The amylin-specific receptor still remains to be identified. Several recent studies have, however, suggested that the identity of an amylin-selective receptor may be determined in part by receptor-activity-modifying proteins (RAMPs) (34).

Example 4

Alteration in Phosphorylation of P20, But Not Its Expression, Is Associated With Insulin Resistance We next investigated the phosphorylation patterns of P20 and the effect of insulin and amylin on this protein in dexamethasone-induced diabetic rats with insulin resistance. The diabetic state of these rats was confirmed by the demonstrated loss of body weight, hyperglycaemia and decrease in insulin-stimulated incorporation of glucose into glycogen (results not shown). In dexamethasone-treated rats, both the fasted basal plasma concentrations of insulin (789±94 pmol/1 vs. 203±28 pmol/1 in control rats) and amylin (144±17 pmol/1 vs. 22.7±5.9 pmol/1 in control rats) were significantly increased (p<0.01 in each case).

Figure 4:
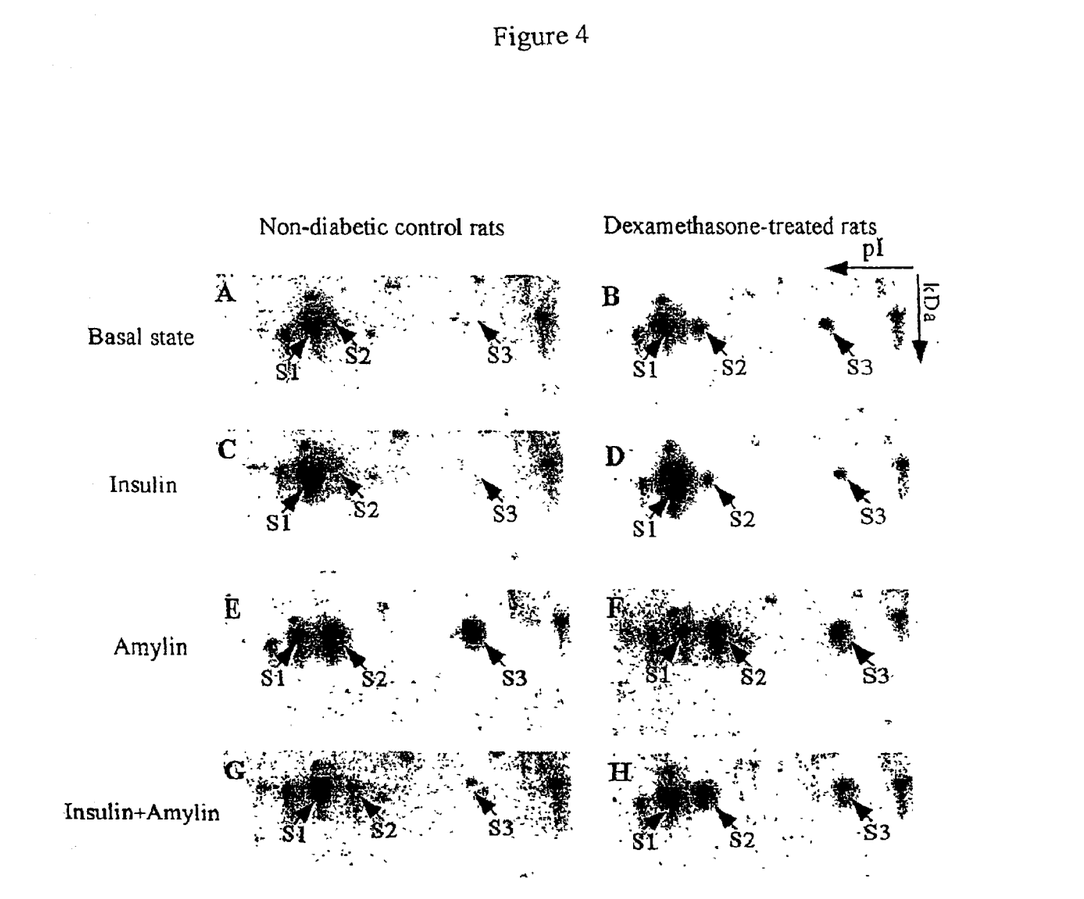
FIG. 4 shows changes in the phosphorylation of P20 and its responsiveness to insulin and amylin in dexamethasone-treated rats with insulin resistance. EDL muscle strips from non-diabetic control rats (left panel) or rats with insulin resistance (right panel) were radiolabelled with $^{32}$P, treated with buffer only (A and B); 50 nM insulin (C and D); 50 nM amylin (E and F); or 50 nM insulin plus 50 nM amylin (G and B) for 30 min. Phosphorylation of P20 was analysed by 2-DE and phosphorimaging. The result is the typical representation of four independent observations.
Figure 5:
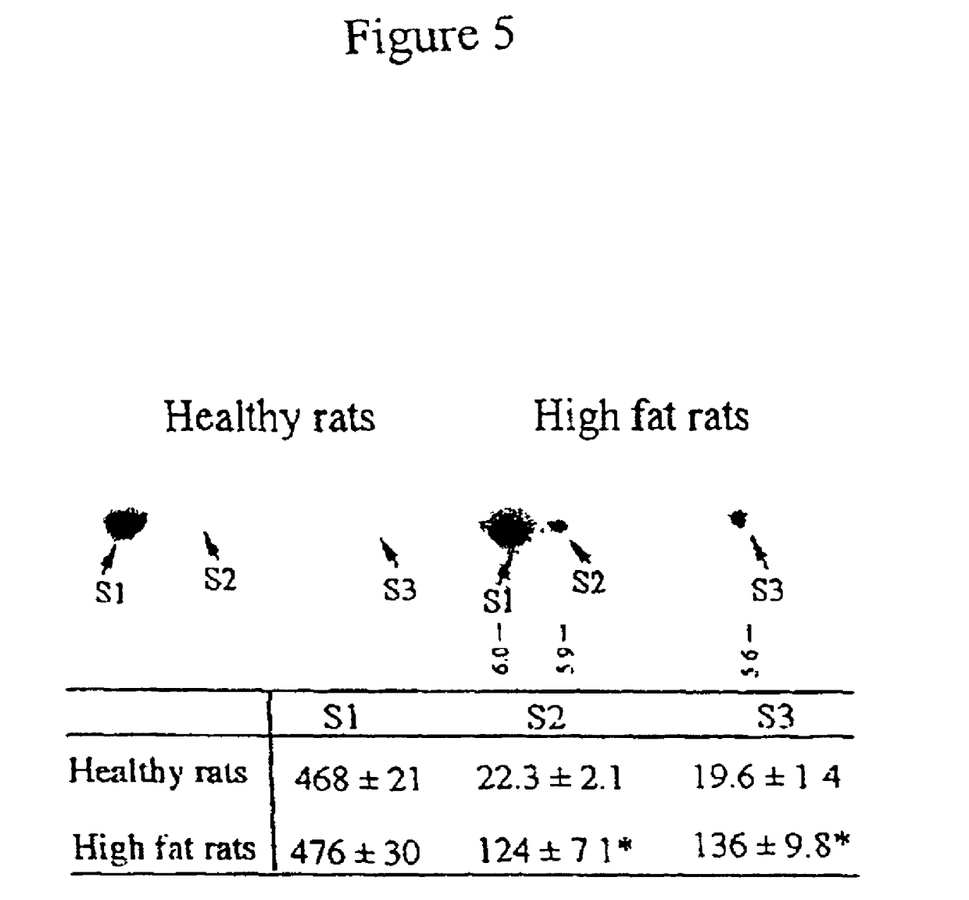
FIG. 5 shows enhanced phosphorylation of S2 and S3 is associated with insulin resistant rats induced by high-fat feeding. 100 μg of proteins from muscle strips from healthy rats or high fat-induced diabetic rats were separated by 2-DE and the three phospho-isoforms of P20 (S1, S2 and S3) was visualised by probing with anti-p20 antibody as described in FIG. 1. The table in the lower panel represents the quantitative analysis for the abundance of each phospho-isoform of P20 in non-diabetic control rats and high fat induced diabetic rats. The abundance of each isoform is expressed as mean PSL values±S.D. * indicates the values that are significantly different (P<0.01) from corresponding values in control rats (n=4).
Figure 6:
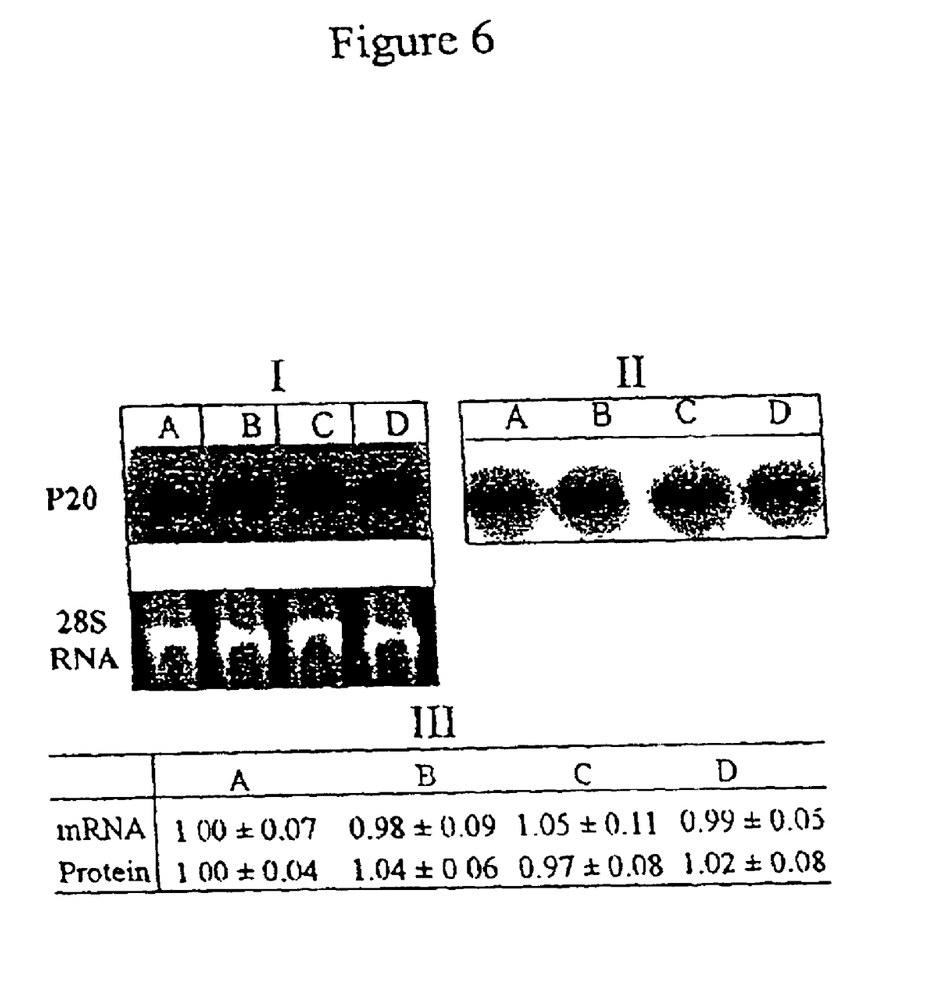

EDL muscle strips from these rats were radiolabelled with $^{32}$P, treated without or with insulin and amylin, then phosphorylation of P20 was analysed by 2-DE and phosphorimaging (FIG. 4). Under the incubation conditions without hormone stimulation, phosphorylation of S2 and S3 was hardly detected in the non-diabetic control rats (FIG. 4A). By contrast, these two phosphoisoforms were clearly visualised in muscle samples from the insulin resistant rats (FIG. 4B). Quantitative analysis by phosphorimager and MacBAS software showed that the signals associated with both S2 and S3 in dexamethasone-treated rats were about 5-fold higher (Table 1). This phenomenon was also observed in a high-fat induced insulin resistant rat model (FIG. 5), suggesting that the increased phosphorylation of two isoforms of P20, S2 and S3, may be associated with insulin resistant states in general. Analysis of P20 expression revealed that the mRNA level and protein abundance of P20 was not changed either in the diabetic rats or in the amylin-treated muscle strips (FIG. 6).

Table 1

Quantitative Analysis of the Radioactivity Associated with the Three Isoforms of P20 in Non-diabetic Control Rats and Dexamethasone-treated Rats.

TABLE 1

Quantitative analysis of the radioactivity associated with the three isoforms of P20 in non-diabetic control rats and dexamethasone-treated rats.

|  | Non-diabetic control rats | | | Dexamethasone-treated rats | | |
|---|---|---|---|---|---|---|
|  | S1 | S2 | S3 | S1 | S2 | S3 |
| Basal state | 434 ± 13 | 21.6 ± 1.9 | 15.1 ± 2.8 | 439 ± 15 | 102 ± 6.2* | 98.6 ± 4.3* |
| Insulin | 831 ± 40 | 20.3 ± 3.4 | 13.3 ± 1.3 | 843 ± 9 | 96.6 ± 5.5* | 92 ± 4* |
| Amylin | 191 ± 9 | 289 ± 20 | 226 ± 17 | 181 ± 11 | 280 ± 13 | 208 ± 15 |
| Insulin + Amylin | 417 ± 16 | 82 ± 4 | 60 ± 4 | 407 ± 21 | 269 ± 16* | 192 ± 15* |

Radio-labelled EDL muscle strips from control and dexamethasone-treated rats were incubated in the absence of hormone (basal state), in the presence of insulin (50 nM), amylin (50 nM) or both hormones. $^{32}$P-labelled isoforms of P20 (S1, S2 and S3) were separated as in FIG. 4, detected using a phosphorimager and analysed by MacBAS software. The radioactivity of each isoform under different treatment is expressed as mean PSL values ± standard deviation.
*indicates values that are significantly different (P < 0.01) from corresponding values in control rats (n = 4).

These results indicate that the increased phosphorylation of S2 and S3 is not due to the increased expression of P20, but rather to a possible defect in the intracellular signal transduction pathways that lead to generation of its phosphorylated isoforms.

Another major alteration in insulin resistant rats is a significant alteration of insulin's ability to inhibit amylin-evoked phosphorylation of S2 and S3. In normal rats, 50 nM insulin decreased phosphorylation of S2 and S3 by 71.6% and 73% respectively, compared to that in samples treated with 50 nM amylin alone (FIGS. 4E and G). In diabetic rats, on the other hand, amylin-evoked phosphorylation of S2 and S3 was little affected by insulin (FIGS. 4F and H). Under this condition, the radioactivity of both S2 and S3 was around 3.3 fold higher than that of the non-diabetic control rats (Table 1).

Insulin resistance is a well-known effect of glucocorticoid excess, but the mechanisms are still uncertain (35). Although muscle is quantitatively the most important tissue for glucose disposal in response to insulin, there are few studies on the effects of glucocorticoids in this tissue. Administration of dexamethasone did not affect the number or affinity of insulin receptors in skeletal muscle but reduced the insulin receptor tyrosine autophosphorylation and also decreased-IRS-1 activation of PI-3 kinase, suggesting the existence of post-receptor defects (36). It has recently been reported that dexamethasone treatment significantly inhibited the insulin-stimulated translocation of GLUT4 from an intracellular pool to the plasma membrane, although expression of this transporter was paradoxically slightly increased (37).

Pieber and coworkers observed that whenever diabetes occurred in dexamethasone-treated rats, the level of amylin and the ratio of amylin/insulin (A/I), were significantly increased (38). The increase in A/I was associated with elevated content of proamylin mRNA relative to proinsulin mRNA. This study implied that amylin could also be an important factor that contributes to the development of dexamethasone-induced insulin resistance. The results of our present study support such a role of amylin. The phosphoisoforms S2 and S3, which were hardly detected in healthy rats but could be induced by amylin, are clearly present in diabetic rats (FIG. 4B). This may be due to the increased amylin level or A/I ratio. It is interesting to note that, in normal rats, insulin specifically suppresses amylin's actions on phosphorylation of P20 and elevation of cAMP levels, but has no detectable effect on the actions of two other catabolic hormones, epinephrine and CGRP (FIG. 3). Such an action of insulin was significantly attenuated in dexamethasone-induced diabetic rats (FIGS. 4F and H). Based on these results, it is tempting to speculate that, under physiological conditions, amylin's antagonism of insulin-stimulated glucose disposal is inhibited by insulin itself. The impairment of this action of insulin may lead to the enhanced catabolic action of amylin, and thus partly contribute to the causation of insulin resistance in dexamethasone-induced diabetic rats.

Example 5

P20 Is Involved In The Regulation Of Glucose Uptake Process In L6 Myotube Cells

Although the physiological role of P20 is uncertain, the high abundance of this protein, and its diverse responsiveness to insulin and its antagonists, suggest that it could be a mediator involved in the biological actions of these metabolic hormones. Notably, P20 has recently been shown to be an actin-binding protein (31). Both cytoskeletal actin filaments and actin-binding proteins have been suggested to play roles in directing traffic of glucose transporters to the cell membrane (39, 40). Interestingly, another two proteins whose increased expression may contribute to insulin resistance in type II diabetes, Rad and PED/PEA-15, are also cytoskeleton-associated proteins involved in the regulation of glucose transport (41, 42). Thus it is intriguing to speculate that metabolic hormones such as insulin and amylin could regulate glucose transport by modulating the phosphorylation states of P20.

To validate this hypothesis, we have established stable transfectants of L6 cells that overexpress P20 (FIG. 7A). Myc-tagged GLUT4 (GLUT4myc) was also co-expressed in these transfectants to increase insulin sensitivity (27). In the myotube cells overexpressing GLUT4myc alone, 50 nM insulin increased 2-deoxyglucose uptake by 2.94±0.31 fold over basal level (FIG. 7B). This insulin-stimulated glucose uptake was decreased by 28% in the presence of 50 nM amylin. However, in cells overexpressing both P20 and GLUT4myc, insulin-stimulated glucose uptake was decreased significantly by 41±3% (n=4, p<0.05), whereas the inhibitory effect of amylin was increased significantly by 24±2% (n=4, p<0.05). This result demonstrated that overexpression of P20 suppresses insulin-stimulated glucose uptake and enhances amylin's ability to inhibit insulin's action in L6 myotubes, suggesting a direct role of this protein in the regulation of glucose metabolism.

Example 6

Summary

In summary, we have recently identified a small phosphoprotein P20 as a common intracellular target for insulin and several of its antagonists including amylin, epinephrine and calcitonin gene-related peptide (CGRP). These hormones elicit phosphorylation of P20 at its different sites, producing three phosphorylated isoforms (S1 with pI value of 6.0, S2 with pI value of 5.9, and S3 with pI value of 5.6) (FEBS Letters 457: 149–152 and 462:25–30, 1999). Here we have shown that P20 is one of the most abundant phosphoproteins in rat EDL muscle. Insulin and amylin, two hormones co-secreted from pancreatic islet β-cells; antagonise each other's actions on phosphorylation of this protein in rat EDL muscle. Insulin inhibited amylin-evoked phosphorylation of S2 and S3, while amylin decreased insulin-induced phosphorylation of S1. In rats made insulin resistant by dexamethasone treatment, the phospho-isoforms S2 and S3, which were barely detected in healthy rats in the absence of hormone stimulation, were significantly increased. Moreover, the ability of insulin to inhibit amylin-evoked phosphorylation of these two isoforms was greatly attenuated. These results suggest that alterations in phosphorylation of P20 could contribute to the development of insulin resistance.

References

1. Moller D E, Flier J S: Insulin resistance—mechanisms, syndromes, and implications. N Engl J Med 325: 938–948, 1991

2. Reaven G M: Pathophysiology of insulin resistance in human disease. Physiol Rev 75: 473–486, 1995

3. Hunter S J, Garvey W T: Insulin action and insulin resistance: diseases involving defects in insulin receptors, signal transduction, and the glucose transport effector system. Am J Med 105: 331–345, 1998

4. Kahn B B: Type 2 diabetes: When insulin secretion fails to compensate for insulin resistance. Cell 92: 593–596, 1998

5. Folli F, Saad M J A, Backer J M, Kahn C R: Regulation of phosphatidylinositol 3-kinase activity in liver and muscle of animal models of insulin-resistant and insulin-deficient diabetes mellitus. J Clin Invest 92: 1787–1794, 1993

6. Bjornholm M, Kawano Y, Lehtihet M, Zierath J R: Insulin receptor substrate-1 phosphorylation and phosphatidylinositol 3-kinase activity in skeletal muscle from NIDDM subjects after in vivo insulin stimulation. Diabetes 46: 524–527, 1997

7. Peraldi P, Spiegelman B: TNF-alpha and insulin resistance: Summary and future prospects. Mol Cell Biochem 182: 169–175, 1998

8. Boden G: Free fatty acids (FFA), a link between obesity and insulin resistance. Front Biosci 3: D169–D175, 1998

9. Cooper G J S, Leighton B, Dimitriadis G D, Parry-Billings M, Kowalchuk J M, Howland K, Rothbard J B, Willis A C, Reid K B M: Amylin found in amyloid deposits in human type 2 diabetes mellitus may be a hormone that regulates glycogen metabolism in skeletal muscle. Proc Natl Acad Sci USA 85: 7763–7766, 1998

10. Leighton B, Cooper G J: Pancreatic amylin and calcitonin gene-related peptide cause resistance to insulin in skeletal muscle in vitro. Nature 335: 632–635, 1988

11. Bjorntorp P: Neuroendocrine perturbations as a cause of insulin resistance. Diabet/Metab Res Rev 15: 427–441, 1999

12. Frontoni S, Choi S B, Banduch D, Rossetti L: In vivo insulin resistance induced by amylin primarily through inhibition of insulin-stimulated glycogen synthesis in skeletal muscle. Diabetes 40: 568–573, 1991

13. Molina J M, Cooper G J S, Leighton B, Olefsky J M: Induction of insulin resistance in-vivo by amylin and calcitonin gene-related peptide. Diabetes 39: 260–265, 1990

14. Castle A L, Kuo C H, Ivy J L: Amylin influences insulin-stimulated glucose metabolism by two independent mechanisms. Am J Physiol 274: E6–E12, 1998

15. Young A A, Wang M W, Cooper G J: Amylin injection causes elevated plasma lactate and glucose in the rat. FEBS Lett 291: 101–104, 1991

16. Young D A, Deems R O, Deacon R W, Mcintosh R H, Foley J E: Effects of amylin on glucose metabolism and glycogenolysis in vivo and in vitro. Am J Physiol 259: E457–E461, 1990

17. Hettiarachchi M, Chalkley S, Furler S M, Choong Y S, Heller M, Cooper G J S, Kraegen E W: Rat amylin (8–37) enhances insulin action and alters lipid metabolism in normal and insulin resistant rats. Am J Physiol 273: E859–E867, 1997

18. Gebre-Medhin S, Mulder H, Pekny M, Westermark G, Tornell J, Westermark P, Sundler F, Ahren B, Betsholtz C: Increased insulin secretion and glucose tolerance in mice lacking islet amyloid polypeptide (amylin). Biochem Biophys Res Commun 250: 271–277, 1998

19. Enoki S, Mitsukawa T, Takemura J, Nakazato M, Aburaya J, Toshimori H, Matsukara S: Plasma islet amyloid polypeptide levels in obesity, impaired glucose tolerance and non-insulin-dependent diabetes mellitus. Diabet Res Clin Prac 15: 97–102, 1992

20. Moller D E, Bjorbaek C, Vidal-Puig A: Candidate genes for insulin resistance. Diabet Care 19: 396–400, 1996

21. DeFronzo R A: Pathogenesis of type 2 diabetes: metabolic and molecular implications for identifying diabetes genes. Diabet Rev 5: 177–269, 1997

22. Kahn C R: Insulin action, diabetogenes, and the cause of type II diabetes. Diabetes 43: 1066–1084, 1994

23. Wang Y, Xu A, Cooper G J S: Amylin evokes phosphorylation of P20 in rat skeletal muscle. FEBS Lett 457: 149–152, 1999

24. Wang Y, Xu A, Pearson R B, Cooper G J: Insulin and insulin antagonists evoke phosphorylation of P20 at serine 157 and serine 16 respectively in rat skeletal muscle. FEBS Lett 462: 25–30, 1999

25. Kato K, Goto S, Inaguma Y, Hasegawa K, Morishita R, Asano T: Purification and characterization of a 20-kDa protein that is highly homologous to alpha B crystalline J Biol Chem 269: 15302–15309, 1994

26. Oakes N D, Cooney G J, Camilleri S, Chisholm D J, Kraegen E W: Mechanisms of liver and muscle insulin resistance induced by chronic high-fat feeding. Diabetes 46: 1768–1774, 1997

27. Robinson R, Robinson L J, James D E, Lawrence J C, Jr.: Glucose transport in L6 myoblasts overexpressing GLUT1 and GLUT4. J Biol Chem 268: 22119–22126, 1993

28. Inaguma Y, Hasegawa K, Kato K, Nishida Y: cDNA cloning of a 20-kDa protein (p20) highly homologous to small heat shock proteins: developmental and physiological changes in rat hindlimb muscles. Gene 178: 145–150, 1996

29. Woodrum D A, Brophy C M, Wingard C J, Beall A, Rasmussen H: Phosphorylation events associated with cyclic nucleotide-dependent inhibition of smooth muscle contraction. Am J Physiol 277: H931–H939, 1999

30. Beall A C, Kato K, Goldenring J R, Rasmussen H, Brophy C M: Cyclic nucleotide-dependent vasorelaxation is associated with the phosphorylation of a small heat shock-related protein. J Biol Chem 272: 11283–11287, 1997

31. Brophy C M, Lamb S, Graham A: The small heat shock-related protein-20 is an actin-associated protein. J Vasc Surg 29: 326–333, 1999

32. Niwa M, Kozawa O, Matsuno H, Kato K, Uematsu T: Small molecular weight heat shock-related protein, HSP20, exhibits an anti-platelet activity by inhibiting receptor-mediated calcium influx. Life Sci 66: L7–L12, 2000

33. Cooper G J S: Amylin compared with calcitonin gene-related peptide: structure, biology, and relevance to metabolic disease. Endocr Rev 15: 163–201, 1994

34. Christopoulos G, Perry K J, Morfis M, Tilakaratne N, Gao Y, Fraser N J, Main M J, Foord S M, Sexton P M: Multiple amylin receptors arise from receptor activity-modifying protein interaction with the calcitonin receptor gene product. Mol Pharmacol 56: 235–242, 1999

35. Andrews R C, Walker B R: Glucocorticoids and insulin resistance: old hormones, new targets. Clin Sci 96: 513–523, 1999

36. Giorgino F, Almahfouz A, Goodyear L J, Smith R J: Glucocorticoid regulation of insulin receptor and substrate IRS-1 tyrosine phosphorylation in rat skeletal muscle in vivo. J Clin Invest 91: 2020–2030, 1993

37. Dimitriadis G, Leighton B, Parry-Billings M, Sasson S, Young M, Krause U, Bevan S, Piva T, Wegener G, Newsholme E A: Effects of glucocorticoid excess on the sensitivity of glucose transport and metabolism to insulin in rat skeletal muscle. Biochem J 321: 707–712, 1997

38. Pieber T R, Stein D T, Ogawa A, Alam T, Ohneda M, McCorkle K, Chen L, McGarry J D, Unger R H: Amylin-insulin relationships in insulin resistance with and without diabetic hyperglycemia. Am J Physiol 265: E446–E453, 1993

39. Kao A W, Noda Y, Johnson J H, Pessin J E, Saltiel A R: Aldolase mediates the association of F-actin with the insulin-responsive glucose transporter GLUT4. J Biol Chem 274: 17742–17747, 1999

40. Tsakiridis T, Vranic M, Klip A: Disassembly of the actin network inhibits insulin-dependent stimulation of glucose transport and prevents recruitment of glucose transporters to the plasma membrane. J Biol Chem 269: 29934–29942, 1994

41. Moyers J S, Bilan P J, Reynet C, Kahn C R: Overexpression of Rad inhibits glucose uptake in cultured muscle and fat cells. J Biol Chem 271: 23111–23116, 1996

42. Condorelli G, Vigliotta G, Iavarone C, Caruso M, Tocchetti C G, Andreozzi F, Cafieri A, Tecce M F, Formisano P, Beguinot L, Beguinot F: PED/PEA-15 gene controls glucose transport and is overexpressed in type 2 diabetes mellitus. EMBO J 17: 3858–3866, 1998

Throughout this application, various publications are referred to by partial citations within parenthesis. Full citations for these publications may be found at the end of the specification. The disclosures of these publications, in their entireties, are hereby incorporated by reference into this application in order to more fully describe the state of the art to which this invention pertains.

It is understood that the examples and embodiments described herein are for illustrative purposes only and that various modifications or changes in light thereof will be suggested to persons skilled in the art and are to be included within the spirit and purview of this application and scope of the appended claims. All publications, patents and patent applications cited herein are hereby incorporated by reference in their entirety for all purposes to the same extent as if each individual publication, patent or patent application were specifically and individually indicated to be so incorporated by reference.

What is claimed is:

1. A method for screening for an agent useful for treatment of insulin resistance comprising contacting a mammalian cell expressing P20 and the agent and determining if the agent suppresses the level of at least one of P20 isoforms S2 and S3, wherein the suppression of S2 and S3 levels is indicative of an agent useful for treatment of insulin resistance.

2. The method of claim 1 wherein the mammalian cell is insulin resistant.

3. The method according to claim 1 wherein the mammalian cell is from a rat or human.

4. The method according to claim 1 wherein the mammalian cell is a myocyte, adipocyte, or skeletal muscle cell.

5. The method of claim 4 wherein the agent is contacted with isolated skeletal muscle.

6. The method of claim 1 wherein the contacting occurs by administration of the agent to an animal.

7. The method of claim 6 wherein the animal is a rodent with genetic or experimentally induced insulin resistance.

8. The method of claim 1 wherein during, prior to, or after contacting the cell and the test agent, the cell is exposed to an amount of amylin, CGRP1, CGRP2, epinephrine or norepinephrine sufficient to induce phosphorylation of P20.

9. The method of claim 1 wherein the cell is exposed to an amount of insulin sufficient to reduce amylin-induced phosphorylation of P20 in a non-insulin resistant cell, during, prior to, or after contacting the cell and the test agent.

10. The method of claim 9 wherein the cell is exposed to insulin ex vivo.

11. A method for screening for an agent useful for treatment of insulin resistance comprising the steps of:
  (a) contacting an insulin resistant mammalian cell expressing P20 and the agent;
  (b) determining an expression level of at least one of P20 isoforms S2 and S3 in the cell; and
  (c) comparing the expression level of S2 and/or S3 to a reference expression level of S2 or S3, wherein said reference expression level is characteristic of (i) expression in a similar cell not exposed to the agent or (ii) expression in a cell that is not insulin resistant,
  and wherein an expression level that is lower than (i) or similar to (ii) indicates the agent is useful for treatment of insulin resistance.

12. The method according to claim 11 wherein the mammalian cell is from a rat or human.

13. The method according to claim 11 wherein the mammalian cell is a myocyte, adipocyte, or skeletal muscle cell.

14. The method of claim 13 wherein the agent is contacted with isolated skeletal muscle.

15. The method of claim 11 wherein the contacting occurs by administration of the agent to an animal.

16. The method of claim 15 wherein the animal is a rodent with genetic or experimentally induced insulin resistance.

* * * * *